US008324125B2

(12) United States Patent
Varma et al.

(10) Patent No.: US 8,324,125 B2
(45) Date of Patent: Dec. 4, 2012

(54) MAGNETIC NANOPARTICLE-SUPPORTED GLUTATHIONE AS A SUSTAINABLE ORGANOCATALYST

(75) Inventors: Rajender S. Varma, Cincinnati, OH (US); Vivek Polshettiwar, Cincinnati, OH (US)

(73) Assignee: The United States of America as represented by the Administrator of the U.S. Environmental Protection Agency, Washington, DC (US)

( * ) Notice: Subject to any disclaimer, the term of this patent is extended or adjusted under 35 U.S.C. 154(b) by 320 days.

(21) Appl. No.: 12/553,681

(22) Filed: Sep. 3, 2009

(65) Prior Publication Data

US 2011/0054180 A1 Mar. 3, 2011

(51) Int. Cl.
*C07F 15/04* (2006.01)
*C07F 15/06* (2006.01)
*C07C 321/04* (2006.01)
*C07D 207/323* (2006.01)
*C07D 401/06* (2006.01)
*C07D 207/325* (2006.01)

(52) U.S. Cl. ............. 502/150; 546/276.4; 562/556; 562/557; 556/138; 548/560; 548/563; 548/561

(58) Field of Classification Search .................. None
See application file for complete search history.

(56) References Cited

U.S. PATENT DOCUMENTS

2009/0068115 A1  3/2009  Gaw et al.

OTHER PUBLICATIONS

Polshettiwar et al. (Chemical Communication, 2009, 1837-1839, Published on Mar. 2, 2009).*
Perez, Iron oxide nanoparticles:Hidden Talent, Nature Nanotech 2007, 535-36.
Polshettiwar et al., The synthesis and applications of a micro-pine-structured nanocatalyst, Chem. Commun. 2008, 6318-20.
Polshettiwar et al., Self-assembly of metal oxides into 3D nano-structures: Synthesis and nano-catalysis, ACS Nano 2009, 3, 728-36.
Latham et al., Controlling Transport and Chemical Functionality of Magnetic Nanoparticles, Acc. Chem. Res. 2008, 41, 411-420.
Hu et al., Magnetically Recoverable Chiral Catalysts Immobilized on Magnetite Nanoparticles for Asymmetric Hydrogenation of Aromatic Ketones, J. Am. Chem. Soc. 2005, 127, 12486-87.
Phan et al., Expanding the Utility of One-Pot Multistep Reaction Networks through Compartmentation and Recovery of the Catalyst, Angew. Chem. Int. Ed. 2006, 45, 2209-12.
Abu-Reziq et al., Metal Supported on Dendronized Magnetic Nanoparticles: Highly Selective Hydroformylation Catalysts, J. Am. Chem. Soc. 2006, 128, 5279-5282.
Shi et al., Tuning Catalytic Activity between Homogeneous and Heterogeneous Catalysis: Improved Activity and Selectivity of Free Nano-Fe2O3 in Selective Oxidations, Angew Chem. Int. Ed. 2007, 46, 8866-68.
Dalaigh et al., A Magnetic-Nanoparticle-Supported 4-N,N-Dialkylaminopyridine Catalyst: Excellent Reactivity Combined with Facile Catalyst Recovery and Recyclability, Angew. Chem. Int. Ed. 2007, 46, 4329-32.
Gleeeson et al., The First Magnetic Nanoparticle-Supported Chiral DMAP Analogue: Highly Enantioselective Acylation and Excellent Recyclability, Chem. Eur. J. 2009, doi- 10.1002/chem.200900532.
Polshettiwar et al., Nanoparticle-supported and magnetically recoverable palladium (Pd) catalyst: a selective and sustainable oxidation protocol with high turnover number, Org. Biomol. Chem., 2009, 7, 37-40.
Polshettiwar et al., Nanoparticle-supported and magnetically recoverable nickel catalyst: a robust and economic hydrogenation and transfer hydrogenation protocol, Green Chem., 2009, 11, 127-131.
Polshettiwar et al., Nanoparticle-Supported and Magnetically Recoverable Ruthenium Hydroxide Catalyst: Efficient Hydration of Nitriles to Amides in Aqueous Medium, Chem. Eur. J. 2009, 15, 1582-1586.
MacMillan, The advent and development of organocatalysis, Nature 2008, 455, 304-308.
Gruttadauria et al., Supported proline and proline-derivatives as recyclable organocatalysts, Chem. Soc. Rev. 2008, 37, 1666-88.
Karimi et al., Asymmetric Organocatalytic Domino Reactions, Angew Chem. Int. Ed. 2007, 46, 7210-7213.
Doyaguez et al., Asymmetric Aldol Reaction Catalyzed by a Heterogenized Proline on a Mesoporous Support. The Role of the Nature of Solvents, J. Org. Chem. 2007, 72, 9353-56.
Chouhan et al., Magnetic nanoparticle-supported proline as a recyclable and recoverable ligand for the CuI catalyzed arylation of nitrogen nucleophiles, Chem. Commun. 2007, 4809-4811.
Brogan et al., Enamine-Based Aldol Organocatalysis in Water: Are They Really "All Wet"?, Angew. Chem. Int. Ed. 2006, 45, 8100-02.

(Continued)

*Primary Examiner* — Melvin C Mayes
*Assistant Examiner* — Yun Qian
(74) *Attorney, Agent, or Firm* — Summa, Additon & Ashe, P.A.

(57) ABSTRACT

This invention relates to the use of nano-organocatalysts, and, more specifically, to the use of magnetic nanomaterial-supported organocatalysts. It is an object of the present invention to provide "green" catalysts and protocols. According to one embodiment of the invention, a nano-organocatalyst in the form of a magnetic nanomaterial-supported organocatalyst is provided. According to other embodiments of the invention, glutathione and cysteine are provided as organocatalysts and magnetic nanomaterial-supported glutathione and magnetic nanomaterial-supported cysteine are provided for use as nano-organocatalysts. According to another embodiment of the invention, a method of using a recyclable magnetic nanomaterial-supported organocatalyst using a totally benign aqueous protocol, without using any organic solvent in the reaction or during the workup, is provided. According to a further embodiment of the invention, a recyclable magnetic nanomaterial-supported organocatalyst for various organocatalytic reactions, including but not limited to Paal-Knorr reactions, aza-Michael addition and pyrazole synthesis, is provided.

10 Claims, 6 Drawing Sheets

OTHER PUBLICATIONS

Hayashi et al., Combined Proline—Surfactant Organocatalyst for the Highly Diastereo- and Enantioselective Aqueous Direct Cross-Aldol Reaction of Aldehydes, Angew Chem. Int. Ed. 2006, 45, 5527-29.

Hayashi et al., Asymmetric Diels—Alder Reactions of a,b-Unsaturated Aldehydes Catalyzed by a Diarylprolinol Silyl Ether Salt in the Presence of Water, Angew Chem. Int. Ed. 2008, 47, 6634-37.

Huang et al., Highly Efficient Asymmetric Direct Stoichiometric Aldol Reactions on/in Water, Angew Chem. Int. Ed. 2007, 46, 9073-77.

Polshettiwar et al., Aqueous microwave chemistry: a clean and green synthetic tool for rapid drug discovery, Chem. Soc. Rev. 2008, 37, 1546-1557.

Ballini et al., 2,5-Dialkylfurans and Nitroalkanes as Source of 2,3,5-Trialkylpyrroles, Synlett 2000, 391-93.

Curini et al., Layered zirconium phosphate and phosphonate as heterogeneous catalyst in the preparation of pyrroles, Tetrahedron Lett. 2003, 44, 3923-25.

Wang et al., Pyrrole synthesis in ionic liquids by Paal-Knorr condensation under mild conditions, Tetrahedron Lett. 2004, 45, 3417-19.

Surendra et al., β-Cyclodextrin promoted aza-Michael addition of amines to conjugated alkenes in water, Tetrahedron Lett. 2006, 47, 2125-27.

Ding et al., Expanding the Scope of Lewis Acid Catalysis in Water: Remarkable Ligand Acceleration of Aqueous Ytterbium Triflate Catalyzed Michael Addition Reactions, J. Org. Chem. 2006, 71, 352-55.

Luo et al., Surfactant-type asymmetric organocatalyst: organocatalytic asymmetric Michael addition to nitrostyrenes in water, Chem. Commun. 2006, 3687-89.

Polshettiwar et al., Tandem bis-aza-Michael addition reaction of amines in aqueous medium promoted by polystyrenesulfonic acid, Tetrahedron Letters 2007, 48, 8735-8738.

Deng et al., Reaction of N-Monosubstituted Hydrazones with Nitroolefins: A Novel Regioselective Pyrazole Synthesis, Org. Lett. 2006, 8, 3505-08.

Polshettiwar et al., Greener and rapid access to bio-active heterocycles: room temperature synthesis of pyrazoles and diazepines in aqueous medium, Tetrahedron Letters 2008, 49, 397-400.

Polshettiwar et al., Magnetic nanoparticle-supported glutathione: a conceptually sustainable organocatalyst, Chem. Commun., 2009, 1837-1839.

Polshettiwar et al., Microwave-Assisted Organic Synthesis and Transformations using Benign Reaction Media, Acc. Chem. Res. 2008, 5, 629-639.

Singh et al., Nanoparticle-based targeted drug delivery, Exp. Mol. Pathology 2009, 86 215-223.

Portney et al., Nano-oncology: drug delivery, imaging, and sensing, Anal. Bioanal. Chem. 2006, 384, 620-630.

Baruwati et al., Bulk synthesis of monodisperse ferrite nanoparticles at water-organic interfaces, J. Phy. Chem. C 2008, 112, 18399-18404.

Basavaiah et al., The Baylis-Hillman reaction: a novel source of attraction, opportunities, and challenges in synthetic chemistry, Chem. Soc. Rev. 2007, 36, 1581-1588.

Beeson et al., Enantioselective Organocatalysis Using SOMO Activation, Science 2007, 316, 582-585.

Blackmond et al., Water in Organocatalytic Processes: Debunking the Myths, Angew. Chem. Int. Ed. 2007, 46, 3798-3800.

Bruckman et al., Organocatalytic reactions: effects of ball milling, microwave and ultrasound irradiation, Green Chem. 2008, 10, 1131-1141.

Clark et al., Self-assembly of orgnocatalysts: fine-tuning orgnocatalytic reactions, Angew. Chem. Int. Ed. 2007, 46, 930-933.

Enders et al., Asymmetric organocatalytic domino reactions, Angew. Chem. Int. Ed. 2007, 46, 1570-1581.

Franzen et al., A General Organocatalyst for Direct a-Functionalization of Aldehydes: Stereoselective C-C, C-N, C-F, C-Br, and C-S Bond-Forming Reactions. Scope and Mechanistic Insights, J. Am. Chem. Soc. 2005, 18296-18304.

Gruttadauria et al., Supported Ionic Liquids. New Recyclable Materials for the I-Proline-Catalyzed Aldol Reaction, Adv. Synth Catal. 2006, 348, 82-92.

Hayashi et al., The Direct and Enantioselective, One-Pot, Three-Component, Cross-Mannich Reaction of Aldehydes, Angew. Chem. Int. Ed. 2003, 42, 3677-3680.

Hayashi et al., Cysteine-Derived Organocatalyst in a Highly Enantioselective Intramolecular Michael Reaction, J. Am. Chem. Soc. 2005, 127, 16028-16029.

Herrera et al., Catalytic Enantioselective Friedel-Crafts Alkylation of Indoles with Nitroalkenes by Using a Simple Thiourea Organocatalyst, Angew. Chem. Int. Ed. 2005, 44, 6576-6579.

Imada et al., Flavin Catalyzed Oxidations of Sulfides and Amines with Molecular Oxygen, J. Am. Chem. Soc. 2003, 125, 2868-2869.

Kazmaier, Amino Acids—Valuable Organocatalysts in Carbohydrate Synthesis, Angew. Chem. Int. Ed. 2003, 44, 2186-2188.

Li et al., Organic chemistry in water, Chem. Soc. Rev. 2006, 35, 68-82.

Liu et al., Organocatalytic and Highly Stereoselective Direct Vinylogous Mannich Reaction, J. Am. Chem. Soc. 2007, 129, 1878-1879.

Liu et al., Asymmetric Direct Aldol Reaction of Functionalized Ketones Catalyzed by Amine Organocatalysts Based on Bispidine, J. Am. Chem. Soc. 2008, 130, 5654-5655.

Lu et al., Magnetic Nanoparticles: Synthesis, Protection, Functionalization, and Application, Angew. Chem. Int. Ed. 2007, 46, 1222-1244.

Masson et al., The Enantioselective Morita-Baylis-Hillman Reaction and Its Aza Counterpart, Angew. Chem. Int. Ed. 2007, 46, 4614-4628.

McCooey et al., Urea- and Thiourea-Substituted Cinchona Alkaloid Derivatives as Highly Efficient Bifunctional Organocatalysts for the Asymmetric Addition of Malonate to Nitroalkenes: Inversion of Configuration at C9 Dramatically Improves Catalyst Performance, Angew. Chem. Int. Ed. 2005, 44, 6367-6370.

Nadagouda et al., Self-assembly of palladium nanoparticles: Synthesis of nanobelts, nanoplates and nanotrees using vitamin B1, and their application in carbon-carbon coupling reactions, J. Mater. Chem. 2009, 19, 2026-2031.

Nicewicz et al., Merging Photoredox Catalysis with Organocatalysis: The Direct Asymmetric Alkylation of Aldehydes, Science 2008, 322, 77-80.

Notz et al., Enamine-Based Organocatalysis with Proline and Diamines: The Development of Direct Catalytic Asymmetric Aldol, Mannich, Michael, and Diels-Alder Reactions, Acc. Chem. Res. 2004, 37, 580-591.

Polshettiwar et al., Tandem Bis-aldol Reaction of Ketones: A Facile One-Pot Synthesis of 1,3-Dioxanes in Aqueous Medium, J. Org. Chem. 2007, 72, 7420-7422.

Polshettiwar et al., Olefin Ring Closing Metathesis and Hydrosilylation Reaction in Aqueous Medium by Grubbs Second Generation Ruthenium Catalyst, J. Org. Chem. 2007, 73, 7417-7419.

Shibuya et al., 2-Azaadamantane N-Oxyl (AZADO) and 1-Me-AZADO: Highly Efficient Organocatalysts for Oxidation of Alcohols, J. Am. Chem. Soc. 2006, 128, 8412-8413.

Xie et al., Organocatalytic Enantioselective Cascade Michael-Alkylation Reactions: Synthesis of Chiral Cyclopropanes and Investigation of Unexpected Organocatalyzed Stereoselective Ring Opening of Cyclopropanes, J. Am. Chem. Soc. 2007, 129, 10886-10894.

* cited by examiner

Where,
R- alkyl ($C_{1-20}$), aryl ($C_{5-25}$), ,
   heterocyclic, -$CH_2CH_2X$ (X - OH, $NH_2$)

$R^1$ - Ph, Cy, 4-ClPh, $PhCH_2$,
   Bu, Et
$R^2$ - Me, *n*-Bu

MAGNETIC NANOPARTICLE-SUPPORTED GLUTATHIONE AS A SUSTAINABLE ORGANOCATALYST

FIELD OF THE INVENTION

Manufacturing protocols can be improved economically and environmentally (made more "green") and made more sustainable through the design and use of catalysts that reduce chemical waste that is harmful to human health and the environment. It is an object of the present invention to provide "green" catalysts and protocols. This invention relates to the use of nano-organocatalysts, and, more specifically, to the use of magnetic nanomaterial-supported organocatalysts.

BACKGROUND OF THE INVENTION

Catalysis lies at the heart of countless chemical protocols, from the academic research laboratories to the chemical industry. A variety of products, such as medicines, fine chemicals, polymers, fibers, fuels, paints, lubricants, and a myriad of other value-added products essential to humans, would not be feasible in the absence of catalysts. These active compounds arbitrate the mechanism by which chemical transformations take place, thus enabling the commercially viable creation of desired materials. A homogeneous catalyst, where the catalyst is in the same phase as the reactants, is often desirable. One attractive property is that all catalytic sites are accessible because the catalyst is generally a soluble metal complex. Furthermore, it is possible to tune the chemo-, regio- and enantioselectivity of the catalyst. Homogeneous catalysts have a number of other advantages such as high selectivities, better yield, and easy optimization of catalytic systems by modification of ligand and metals. They are widely used in a number of commercial applications, but the difficulty of catalyst separation from the final product creates growing economic and environmental barriers to broaden their scope.

Despite the advantages of homogeneous catalytic systems and their wide use in a number of applications, many homogeneous catalytic systems have not been commercialized because of the difficulty encountered in separating the catalyst from final reaction product and the solvent. Removal of trace amounts of catalyst from the end product is essential since metal contamination is highly regulated especially by the pharmaceutical industry. Even with the extensive and careful use of various techniques such as distillation, chromatography, or extraction, removal of trace amounts of catalyst remains a challenge.

Heterogeneous catalyst systems appear to be the best logical solution to overcome the separation problems in homogeneous catalysis. The majority of the novel heterogenised catalysts are based on silica supports, primarily because silica displays some advantageous properties, such as excellent stability (chemical and thermal), good accessibility, porosity, and the fact that organic groups can be robustly anchored to the surface to provide catalytic centers. The common structural feature of these materials is the entrapment or anchoring of the dopant (catalytic) molecule in the pores of silica, a phenomenon which imparts unique chemical and physical properties to resulting hybrid silica. Anchoring can be achieved by covalent binding of the molecules or by simple adsorption; however covalent anchoring is robust enough to withstand the harsh reaction conditions and the catalyst can be reused several times. A vast majority of the industrial heterogeneous catalysts are high-surface-area solids onto which an active component is dispersed or attached.

Although attempts have been made to make all active sites on solid supports accessible for reaction, allowing rates and selectivities comparable to those obtained with homogeneous catalysts, only sites on the surface are available for catalysis thus decreasing the overall reactivity of the catalyst system. Another problem is the leaching of active molecule/complex from solid supports because of breaking of bonds between metal and ligand during catalytic reactions, which again necessitates separation of trace metals from final product. Catalyst recovery is often performed by filtration that reduces efficiency, and extractive isolation of products requires large amounts of organic solvents.

Consequently, new catalyst systems that allow for the rapid, selective chemical transformations with excellent product yield coupled with the ease of catalyst separation and recovery are much sought for "greening" the chemical manufacturing processes.

Nanomaterials, including nanoparticles, have emerged as sustainable alternatives to conventional materials, as robust, high-surface-area heterogeneous catalyst and catalyst supports. The nano-size of the particles increases the exposed surface area of active component of catalyst thereby enhancing the contact between reactants and catalyst dramatically and mimicking the homogeneous catalysts. The scientific challenge is the synthesis of catalyst in nano-size to allow facile movement of materials in the reacting phase and control over morphology of nanostructures to tailor the physical and chemical properties. The development of solution-based controlled synthesis of nanomaterials has made this possible without difficulty. *Synthesis of single-crystal micro-pine structured nano-ferrites and their application in catalysis*, Polshettiwar et al., Chem. Commun. 2008, 6318; *Self-assembly of metal oxides into 3D nano-structures: Synthesis and nano-catalysis*, Polshettiwar et al, ACS Nano. 2009, 3, 728.

Magnetic nanomaterials are envisaged to have major impacts on catalysis and many other areas, such as medicine, drug delivery and remediation. These inexpensive materials are accessible via simple synthesis and they can be easily enhanced/tuned by postsynthetic surface modifications. *Controlling Transport and Chemical Functionality of Magnetic Nanoparticles*, Latham et al., Acc. Chem. Res. 2008, 41, 411-420. Functionalized nanoparticles have emerged as feasible substitute to conventional materials as a robust, active, high-surface-area catalyst support. *Magnetically Recoverable Chiral Catalysts Immobilized on Magnetite Nanoparticles for Asymmetric Hydrogenation of Aromatic Ketones*, Hu et al, J. Am. Chem. Soc. 2005, 127, 12486-87; *Expanding the Utility of One-Pot Multistep Reaction Networks through Compartmentation and Recovery of the Catalyst*, Phan et al., Angew. Chem. Int. Ed. 2006, 45, 2209-12; *Metal Supported on Dendronized Magnetic Nanoparticles: Highly Selective Hydroformylation Catalysts*, Abu-Reziq et al., J. Am. Chem. Soc. 2006, 128, 5279-5282; *Tuning Catalytic Activity between Homogeneous and Heterogeneous Catalysis Improved Activity and Selectivity of Free Nano-$Fe_2O_3$ in Selective Oxidations*, Shi et al., Angew Chem. Int. Ed. 2007, 46, 8866-68; *A Magnetic-Nanoparticle-Supported 4-N,N-Dialkylaminopyridine Catalyst: Excellent Reactivity Combined with Facile Catalyst Recovery and Recyclability*, Dalaigh et al., Angew. Chem. Int. Ed. 2007, 46, 4329-32; *The First Magnetic Nanoparticle-Supported Chiral DMAP Analogue: Highly Enantioselective Acylation and Excellent Recyclability*, Gleeson et al. Chem. Eur. J. 2009, doi-10.1002/chem. 200900532. In view of their nano-size, the contact between reactants and catalyst increases dramatically, thus mimicking the homogeneous catalysts. They offer an added advantage of being magnetically separable, thereby eliminating the requirement of catalyst filtration after completion of the reaction. *Nanoparticle-supported and magnetically recoverable palladium (Pd) catalyst: a selective and sustainable oxidation protocol with high turnover number*, Polshettiwar et. al. *Org. Biomol. Chem.*, 2009, 7, 37-40; *Nanoparticle-supported and magnetically recoverable nickel catalyst: a robust and economic hydrogenation and transfer hydrogenation protocol*, Polshettiwar et. al. *Green Chem.*, 2009, 11, 127-131; *Nanoparticle-Supported and Magnetically Recoverable Ruthenium Hydroxide Catalyst: Efficient Hydration of Nitriles to Amides in Aqueous Medium*, Polshettiwar et. al. Chem. Eur. J. 2009, 15, 1582-1586.

During the past decade, organocatalysis, a metal-free approach to the synthesis of organic molecules, has become a significant area of research. A diverse set of reactions, including enantioselective C—C, C—N, C—O bond formation, Diels-Alder, Baylis-Hilman, Mannich, Michael, Friedel-Crafts alkylation, oxidation, and carbohydrate synthesis, has benefited from the developments in this area. *The advent and development of organocatalysis*, MacMillan, Nature 2008, 455, 304-308. This relatively green approach has been rendered even greener by efforts in immobilization and recycling of the organocatalysts on supports, which involve their adsorption, covalent linkage, and dissolution in various matrices. *Supported proline and proline-derivatives as recyclable organocatalysts*, Gruttadauria et al., *Chem. Soc. Rev.* 2008, 37, 1666-88; *Asymmetric Organocatalytic Domino Reactions*, Karimi et al., *Angew Chem. Int. Ed.* 2007, 46, 7210-7213; *Asymmetric Aldol Reaction Catalyzed by a Heterogenized Proline on a Mesoporous Support. The Role of the Nature of Solvents*, Doyaguez et al., *J. Org. Chem.* 2007, 72, 9353-56; *Magnetic nanoparticle-supported proline as a recyclable and recoverable ligand for the CuI catalyzed arylation of nitrogen nucleophiles*, Chouhan et al. Chem. Commun. 2007, 4809-4811. Newer strategies include the use of non-traditional methods such as light, mechanochemical mixing, microwave (MW), and ultrasonic irradiation. Most of these reactions are generally carried out in organic solvents, with a few aqueous phase organocatalytic processes as recent exceptions. *Enamine-Based Aldol Organocatalysis in Water: Are They Really "All Wet"?*, Brogan et al., *Angew. Chem. Int. Ed.* 2006, 45, 8100-02; *Combined Proline-Surfactant Organocatalyst for the Highly Diastereo- and Enantioselective Aqueous Direct Cross-Aldol Reaction of Aldehydes*, Hayashi et al., *Angew Chem. Int. Ed.* 2006, 45, 5527-29; *Asymmetric Diels-Alder Reactions of a,b-Unsaturated Aldehydes Catalyzed by a Diatylprolinol Silyl Ether Salt in the Presence of Water*, Hayashi et al., Angew Chem. Int. Ed. 2008, 47, 6634-37; *Highly Efficient Asymmetric Direct Stoichiometric Aldol Reactions on/in Water*, Huang et al., *Angew Chem. Int. Ed.* 2007, 46, 9073-77. Although water is an environmental benign solvent, and addition of water often accelerates the reaction, isolation of final organic product from a reaction mixture is often tedious. Most of the reactions described in published reports use excessive amounts of toxic organic solvents for workup and the total amount of water used in the process is much less. Environmental and economic aspects of both the reaction step and the product workup stage are important and are key to determining the greenness of aqueous protocols.

The efficiency of MW flash-heating has resulted in dramatic reductions in reaction times, reduced from days to minutes, which is potentially important in process chemistry for the expedient generation of fine chemicals. *Microwave-Assisted Organic Synthesis and Transformations using Benign Reaction Media*, Polshettiwar et. al. Acc. Chem. Res. 2008, 5, 629-639. Microwaves initiate rapid intense heating of polar molecules such as water while non-polar molecules do not absorb the radiation and in turn not heated. It was also established that the use of water was advantageous in microwave chemistry and expedited the protocol with more energy efficiency. Selective heating can also be exploited in heterogeneous catalysis protocols. *Aqueous microwave chemistry: a clean and green synthetic tool for rapid drug discovery*, Polshettiwar et. al. Chem. Soc. Rev. 2008, 37, 1546-1557.

The nano-supported, magnetically recyclable organocatalysts of embodiments of the present invention may be used for various organocatalytic reactions, including but not limited to Paal-Knorr reactions, aza-Michael additions and pyrazole synthesis.

The Paal-Knorr reaction in which amines are converted to pyrrole in one step has gained great interest in the synthetic organic chemistry because these heterocycles are intermediates for various pharmaceutical drugs. A range of clean protocols has been developed by using solid supported catalysts such as alumina, zeolites, phosphates, and ionic liquids. *2,5-Dialkylfurans and Nitroalkanes as Source of 2,3,5-Trialkylpyrroles*, Ballini et al., *Synlett* 2000, 391-93; *Layered zirconium phosphate and phosphonate as heterogeneous catalyst in the preparation of pyrroles*, Curini et al., *Tetrahedron Lett.* 2003, 44, 3923-25; *Pyrrole synthesis in ionic liquids by Paal-Knorr condensation under mild conditions*, Wang et al., *Tetrahedron Lett.* 2004, 45, 3417-19. The use of non-conventional energy sources such as microwave and ultrasound has also been studied. However, most of the above methods involve the use of excess amounts of catalyst, toxic organic solvents and tedious workup and cannot be considered as real green protocols. Further, the inventors are not aware that this reaction has ever been accomplished using an organocatalyst.

Aza-Michael addition is a vital carbon-nitrogen bond-forming reaction and has been intensively examined as a powerful tool in organic synthesis. However, most of the aza-Michael additions are performed in organic solvents. Recently β-cyclodextrin, ytterbium triflate, surfactant-type asymmetric organocatalyst (STAO) type catalyst and polystyrenesulfonic acid, have been used in aqueous medium. *β-Cyclodextrin promoted aza-Michael addition of amines to conjugated alkenes in water*, Surendra et al., *Tetrahedron Lett.* 2006, 47, 2125-27; *Expanding the Scope of Lewis Acid Catalysis in Water: Remarkable Ligand Acceleration of Aqueous Ytterbium Triflate Catalyzed Michael Addition Reactions*, Ding et al., *J. Org. Chem.* 2006, 71, 352-55; *Surfactant-type asymmetric organocatalyst: organocatalytic asymmetric Michael addition to nitrostyrenes in water*, Luo et al., *Chem. Commun.* 2006, 3687-89; *Tandem bis-aza-Michael addition reaction of amines in aqueous medium promoted by polystyrenesulfonic acid*, Polshettiwar et al. Tetrahedron Letters 2007, 48, 8735-8738. Although today's environmental concerns encourage the development of such greener synthetic methodology in aqueous medium, many of these methods suffer from limitations such as the use of expensive and toxic catalysts and harsh reaction conditions.

Pyrazoles are an important class of bio-active drug targets in the pharmaceutical industry, in both lead identification and lead optimization processes. Recently, several efficient methods have been developed (*Reaction of N-Monosubstituted Hydrazones with Nitroolefins: A Novel Regioselective Pyrazole Synthesis*, Deng et al., *Org. Lett.* 2006, 8, 3505-08 and references cited therein, *Greener and rapid access to bio-active heterocycles: room temperature synthesis of pyrazoles and diazepines in aqueous medium*, Polshettiwar et al. Tetrahedron Letters 2008, 49, 397-400); however most of these utilize a circuitous route requiring longer reaction times, and are often conducted in organic solvents. Although organocatalysis has been extensively explored, much remains to be accomplished, especially in the context of a truly sustainable protocol.

Thus, there is a need for "green" catalysts and, further, a need for benign aqueous protocols that do not use any organic solvent in the reaction or during the workup.

BRIEF SUMMARY OF THE INVENTION

It is an object of the present invention to provide "green" catalysts and protocols. According to one embodiment of the invention, a nano-organocatalyst in the form of a magnetic nanomaterial-supported organocatalyst is provided, wherein an organocatalyst is anchored to a magnetic nanomaterial. According to one embodiment of the invention, a magnetic nanomaterial-supported organocatalyst for various organocatalytic reactions, including but not limited to Paal-Knorr reactions, aza-Michael addition and pyrazole synthesis, is provided. According to another embodiment of the invention, a method of catalyzing a reaction using a magnetic nanomaterial-supported organocatalyst comprises the steps of providing a magnetic nanomaterial-supported organocatalyst, wherein an organocatalyst is anchored to a magnetic material, providing a reagent composition, and contacting the magnetic nanomaterial-supported organocatalyst with the reagent composition.

A nano-organocatalyst according to one embodiment of the invention is formed when surfaces of magnetic nanomaterial are modified by anchoring an organocatalyst to the nanomaterial to functionalize the nanomaterial. According to another embodiment of the invention, the organocatalyst comprises a compound having a thiol group, and as shown in FIG. 1, after sonication, the organocatalyst is anchored to the magnetic nanomaterial through a sulfur group, thereby forming the nano-organocatalyst. According to other embodiments of the invention, glutathione or cysteine is selected as the organocatalyst and anchored to the magnetic nanomaterial through the sulfur group, thereby imparting desirable chemical functionality. In accordance with other embodiments, recyclable magnetic nanomaterial-supported glutathione and recyclable magnetic nanomaterial-supported cysteine are provided for use as nano-organocatalysts.

According to another embodiment of the invention, a method of using a magnetic nanomaterial-supported organocatalyst using a totally benign aqueous protocol, without using any organic solvent in the reaction or during the workup, is provided. According to one embodiment of the invention, the magnetic nano-organocatalyst may be separated from a reaction mixture using an external magnet, eliminating the requirement of catalyst filtration. According to further embodiments of the invention, magnetic nanomaterial-supported organocatalysts as described herein are recyclable.

The foregoing, as well as other characteristics and advantages of the invention and the manner in which the same are accomplished, are further specified within the following detailed description and its accompanying drawings.

DETAILED DESCRIPTION OF THE INVENTION

Development in the area of supported organocatalysts will encourage the production of fine chemicals in a sustainable manner worldwide. According to one embodiment of the invention, a nano-organocatalyst in the form of a magnetic nanomaterial-supported organocatalyst is provided. Surfaces of magnetic nanomaterial may be modified by anchoring organocatalysts to the nanomaterial to functionalize the nanomaterial. In one embodiment, nano-organocatalysts are formed by anchoring benign organocatalysts to magnetic nanomaterial in a manner that keeps active sites free for catalysis. Another embodiment of the invention provides a nano-organocatalyst comprising a magnetic nanomaterial-supported organocatalyst, wherein an organocatalyst comprises a compound having a thiol group, and further wherein the organocatalyst is anchored to a magnetic nanomaterial via sonication through a sulfur group to functionalize the magnetic nanomaterial. According to other embodiments of the invention, the compound having a thiol group is selected from the group consisting of glutathione and cysteine. Embodiments of the invention are also described in *Magnetic nanoparticle-supported glutathione: a conceptually sustainable organocatalyst*, Polshettiwar et. al. *Chem. Commun.*, 2009, 1837-1839, incorporated herein by reference.

Glutathione is a highly benign tripeptide consisting of glutamic acid, cysteine and glycine units and is a ubiquitous antioxidant present in human and plant cells. Besides a thiol group, each molecule also contains amine and carboxylate functionalities that provide coupling possibilities for further cross-linking to other molecules. Glutathione and cysteine are benign compounds that each have highly reactive thiol groups. According to other embodiments of the invention, glutathione and cysteine are provided as organocatalysts, and nano-organocatalysts in the form of magnetic nanomaterial-supported glutathione and magnetic nanomaterial-supported cysteine are provided. Surfaces of magnetic nanomaterials may be modified by anchoring glutathione or cysteine thereon, thereby imparting desirable chemical functionality. Glutathione and cysteine may be anchored to the nanomaterial by sulfur groups, keeping active sites free for catalysis.

Figure 1:
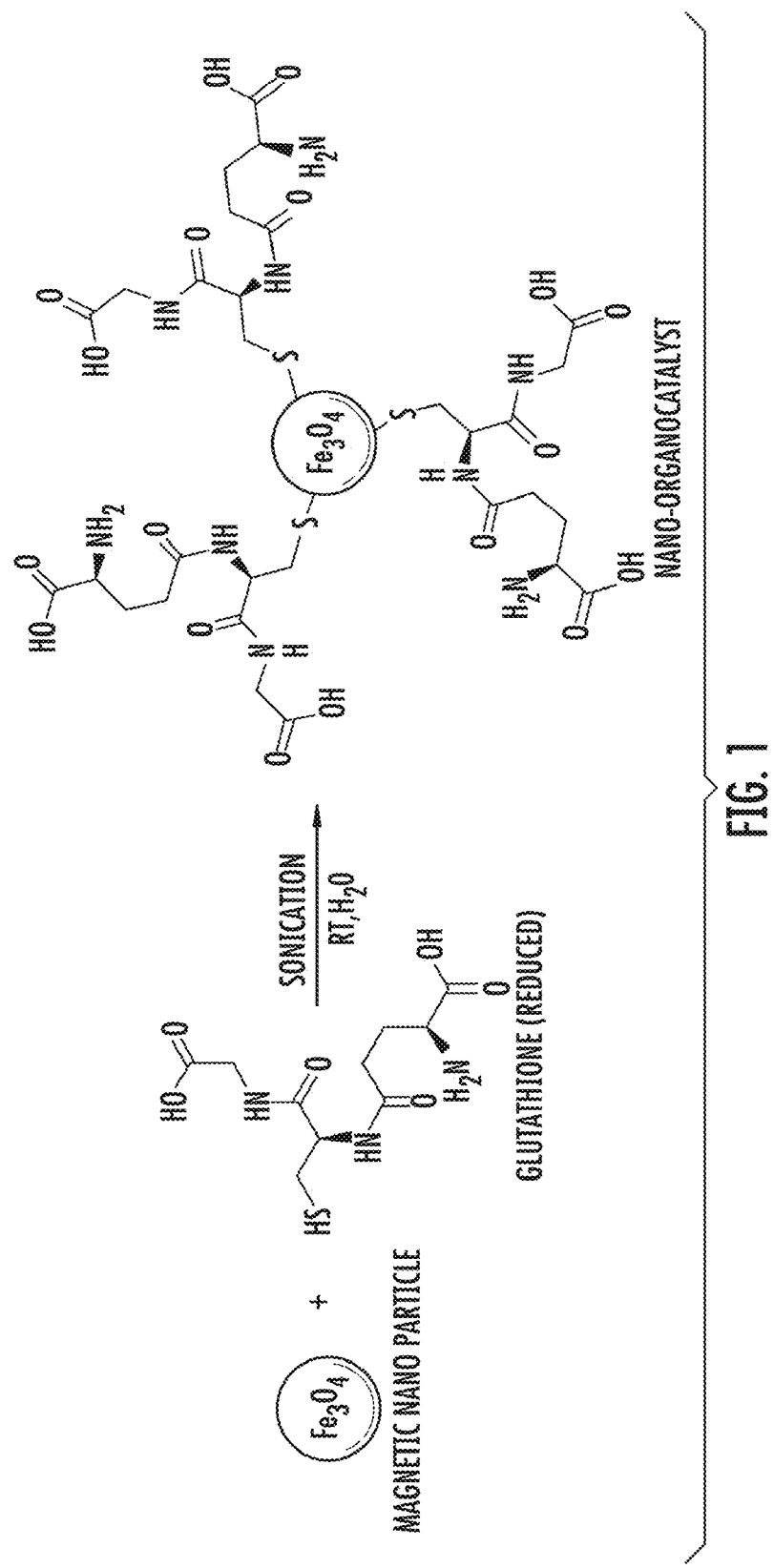
FIG. 1 illustrates the synthesis of magnetic nanoparticle-supported glutathione, according to one embodiment of the invention.

Postsynthetic surface modification of magnetic nanomaterial, including but not limited to nanoparticles, by glutathione or cysteine imparts desirable chemical functionality and enables the generation of catalytic sites on the surfaces of ensuing nano-organocatalysts. One embodiment of the invention provides a nano-organocatalyst comprising magnetic nanomaterial-supported glutathione, wherein glutathione is anchored to magnetic nanomaterial via a sulfur group as shown in FIG. 1 to functionalize the magnetic nanomaterial. Another embodiment of the invention provides a nano-organocatalyst comprising magnetic nanomaterial-supported cysteine, wherein cysteine is anchored to magnetic nanomaterial to functionalize the magnetic nanomaterial.

According to another embodiment of the invention, the magnetic nanomaterial is selected from the group consisting of nano-ferrite, nano-nickel ferrite, nano-cobalt ferrite, nano-iron, and nano-cobalt and their bimetallic derivatives. According to a further embodiment of the invention, the magnetic nanomaterial comprises magnetic nanoparticles, and according to another embodiment, the magnetic nanomaterial comprises nano-ferrite in the form of nanoparticles.

The nano-organocatalyst of the invention may be prepared in high yield using the post-functionalization method described in *Magnetic nanoparticle-supported glutathione: conceptually sustainable organocatalyst*, Polshettiwar et. al. *Chem. Commun.*, 2009, 1837-1839; *The synthesis and applications of a micro-pine-structured nanocatalyst*, Polshettiwar et al., *Chem. Commun.* 2008, 6318-20 and *Self-assembly of metal oxides into 3D nano-structures: Synthesis and nanocatalysis*, Polshettiwar et al., *ACS Nano* 2009, 3, 728-36, each of which is incorporated herein by reference.

The synthesis of nanoparticle-supported glutathione as a nano-organocatalyst, according to one embodiment of the invention, is illustrated in FIG. 1. This nano-organocatalyst may be prepared by sono-chemical covalent anchoring of glutathione molecules through coupling of a sulfur group and free hydroxyl groups of ferrite surfaces. As shown in FIG. 1, nano-$Fe_3O_4$, a magnetic nanoparticle, is combined with glutathione (reduced) with water and sonicated at room temperature. In the resulting nano-organocatalyst, glutathione is attached to the magnetic nanoparticle by a sulfur group, leaving the terminal carboxylic acid groups free for catalysis.

According to one embodiment of the invention, synthesis of a nano-organocatalyst is accomplished by anchoring to a magnetic nanomaterial, through a sulfur group, an organocatalyst comprising a compound having a thiol group. According to another embodiment of the invention, the organocatalyst is selected from the group consisting of glutathione and cysteine. According to a further embodiment of the invention, the magnetic nanomaterial is selected from the group consisting of nano-ferrite, nano-nickel ferrite, nano-cobalt ferrite, nano-iron, and nano-cobalt and their bimetallic derivatives.

Figure 2:
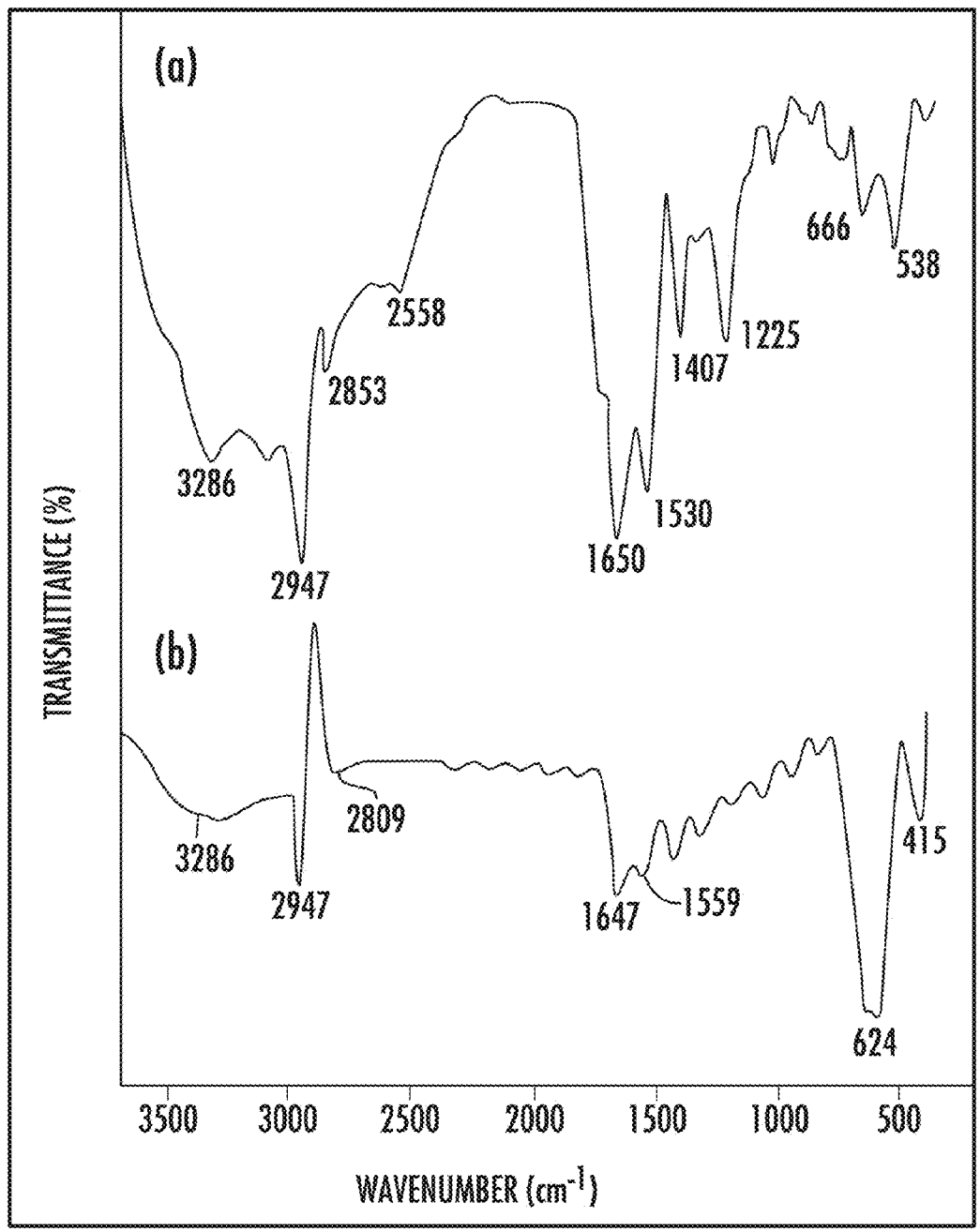
FIG. 2 depicts the FT-IR spectra of (a) glutathione and (b) magnetic nanoparticle-supported glutathione of one embodiment of the invention.
Figure 3:
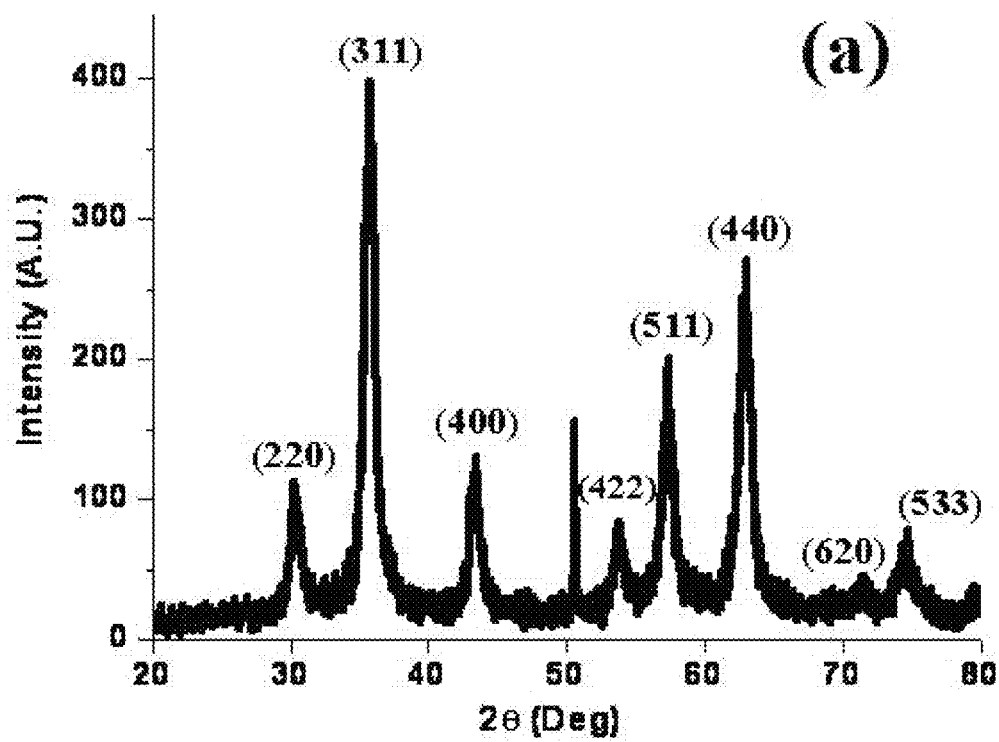
FIG. 3 depicts a powder X-ray diffraction (XRD) pattern for a magnetic nanoparticle-supported glutathione according to one embodiment of the invention.
Figure 4:
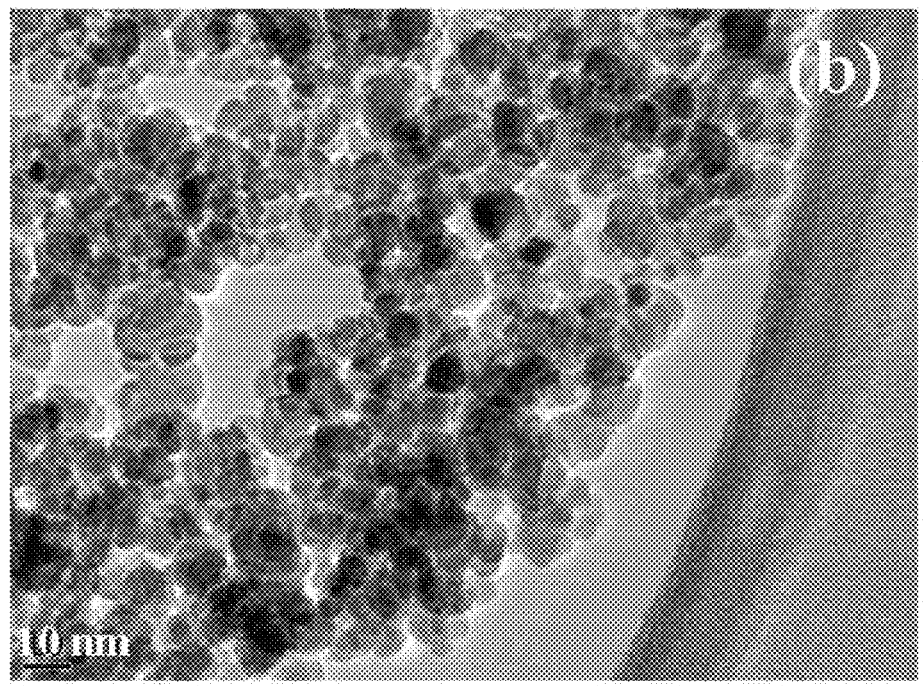
FIG. 4 depicts the TEM image of as-synthesized magnetic nanoparticle-supported glutathione, according to one embodiment of the invention.

According to one embodiment of the invention, a nanoparticle-supported glutathione was synthesized as follows: Nano-$Fe_3O_4$ (0.5 gm) was dispersed in 15 mL water and 5 mL methanol and sonicated for 15 minutes. Glutathione (reduced form) (0.4 gm) dissolved in 5 mL water was added to this solution and again sonicated for 2 hours. The nanoparticle-supported glutathione (the nano-organocatalyst) was then isolated by centrifugation, washed with water and methanol, and dried under vacuum at 50° C. to 60° C. Anchoring of glutathione on the surface of the resulting nano-organocatalyst was confirmed through examination by FT-IR spectroscopy, as shown in FIG. 2. The FT-IR spectra for glutathione is identified as spectra (a) of FIG. 2; the FT-IR spectra for the magnetic nanoparticle-supported glutathione as synthesized above is identified as spectra (b) of FIG. 2. Three characteristic bands (2947 $cm^{-1}$ (C—H stretching), 1648 $cm^{-1}$ (cysteine-carbonyl), and 1629 $cm^{-1}$ (glutamic acid-carbonyl) confirmed the attachment of glutathione on nano-ferrite surfaces. The molecule was firmly anchored via a sulfur group, as the IR band at 2558 $cm^{-1}$ for S—H stretching was diminished in the catalyst. A strong absorption band at 592 $cm^{-1}$ was due to the vibration of the Fe—O bond of ferrite. The crystalline structures of the organocatalyst were determined by powder X-ray diffraction (XRD), as shown in FIG. 3; the diffraction patterns and relative intensities of all the peaks matched well with those of magnetite (JCPDS card no. 00-002-1035). Other oxide or hydroxide phases were not observed and the broad XRD peaks clearly indicate the nanocrystalline nature of the material. As shown in FIG. 4, transmission electron microscopy (TEM) analysis of the organocatalyst showed uniform-sized particles with spherical morphology with an average size range of 10-12 nm. This is comparable to the crystallite size (10.11 nm) calculated from X-ray spectrum using Scherer formula for the full width at half-maximum (fwhm) of the (311) reflection.

The strategy of the invention of immobilization of various organic molecules on magnetic nano-support can also be used for designing novel sensors, circuits, and devices on the nano-scale. This system can also be used for drug delivery, medical imaging, magnetic field assisted transport, separations and analyses. Nanoparticle-based targeted drug delivery, Singh et. al. Exp. Mol. Pathology. 2009, 86 215-223, *Nano-oncology: drug delivery, imaging, and sensing*, Portney et. al. Anal. Bioanal. Chem. 2006, 384, 620-630, incorporated herein by reference.

Reactions may be catalyzed using the magnetic nanomaterial-supported organocatalyst of embodiments of the invention described herein. According to another embodiment of the invention, a method of catalyzing a reaction using a magnetic nanomaterial-supported organocatalyst comprises the steps of: providing a magnetic nanomaterial-supported organocatalyst, wherein an organocatalyst is anchored to the magnetic nanomaterial; providing a reagent composition; and contacting the magnetic nanomaterial-supported organocatalyst with the reagent composition. According to a further embodiment, the method includes a step of separating the magnetic nanomaterial-supported organocatalyst from a reaction product with a magnet. According to one embodiment of the invention, the organocatalyst comprises a compound having a thiol group and the organocatalyst is anchored to the magnetic nanomaterial through a sulfur group after sonication. According to other embodiments of the invention, the organocatalyst comprises glutathione or cysteine. According to another embodiment of the invention, the magnetic nanomaterial is selected from the group consisting of nano-ferrite, nano-nickel ferrite, nano-cobalt ferrite, nano-iron, and nano-cobalt and their bimetallic derivatives. According to another embodiment, the magnetic nanomaterial comprises nano-ferrite in the form of nanoparticles.

Although the nano-organocatalysts of the invention may be used with organic solvents, according to one embodiment of the invention, a nano-organocatalyst assisted reaction is conducted in a benign solution comprising water, polyethylene glycol, or a mixture thereof. Another embodiment of the invention is a method of catalyzing a reaction wherein a magnetic nanomaterial-supported organocatalyst and reagent composition are contacted in an aqueous medium.

Separation of the catalyst and isolation of products are the main operations in aqueous organocatalysis. Catalyst recovery is often performed by filtration that reduces efficiency, and extractive isolation of products requires large amount of organic solvents. According to another embodiment of the invention, a method of using a recyclable magnetic nanomaterial-supported organocatalyst using a totally benign aqueous protocol, without using any organic solvent in the reaction or during the workup, is provided. According to one embodiment of the invention, a method of catalyzing a reaction comprises a step of separating the magnetic nanomaterial-supported organocatalyst from a reaction product with a magnet. When phase separation of the desired reaction product from the aqueous media occurs, the isolation of crude product by simple decantation rather than tedious extraction processes is facilitated. In cases in which solid product precipitates out, the product may then be isolated by simple filtration after removal of the nano-organocatalyst. Consequently, the use of volatile organic solvents may be reduced during product workup.

According to another embodiment of the invention, the nano-organocatalyst may be used under MW irradiation conditions. The efficiency of MW flash-heating has resulted in dramatic reductions in reaction times, reduced from days to minutes, which is potentially important in process chemistry for the expedient generation of fine chemicals. Microwave heating depends on composition and structure of molecules (i.e. their dielectric properties) and this property can facilitate selective heating. MW-assisted chemistry allows rapid heating of a reaction mixture to required temperatures and allows the precise control of the reaction temperature as a result of the efficiency of the interaction of MWs with the polar nano-catalyst. The magnetic nanomaterial-supported organocatalysts may also act as susceptors, materials that efficiently absorb microwave irradiation and transfer the generated thermal energy to molecules in the vicinity that are weak microwave absorber. Because MW-assisted reactions are rapid, the residency time of nano-catalyst at high temperature is minimum. Catalytical processes with such shorter reaction times safeguard the catalyst from deactivation and decomposition, consequently increasing the overall competence of catalyst as well as entire protocol. It appears that this approach of fusing MW technique with nano-catalysis and benign water (as a reaction medium) can offer an extraordinary synergistic effect with greater potential than these three individual components in isolation.

Figure 5:
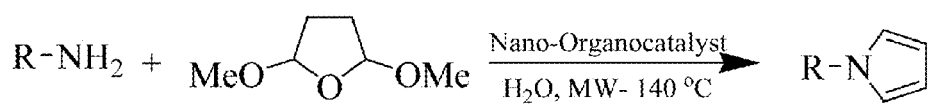
FIG. 5 illustrates nano-organocatalyst promoted Paal-Knorr reactions according to one embodiment of the invention.

According to another embodiment of the invention, a recyclable magnetic nanomaterial-supported organocatalyst for various organocatalytic reactions, including but not limited to Paal-Knorr reactions, aza-Michael addition and pyrazole synthesis, is provided. According to one embodiment of the invention, nano-organocatalysts are used in connection with Paal-Knorr reactions in which amines are converted to pyrrole in one step. To the best of the inventors' knowledge, Paal-Knorr reactions have never before been accomplished using an organocatalyst. The nano-organocatalyst promoted Paal-Knorr reactions are illustrated in FIG. 5. In these reactions, an amine is combined with tetrahydro-2,5-dimethoxyfuran. The nano-organocatalysts of embodiments of the invention display high catalytic activity for Paal-Knorr reactions and a variety of amines react efficiently with tetrahydro-2,5-dimethoxyfuran to afford the desired pyrrole derivates in good yields. The rates were essentially the same for both the aliphatic or aromatic nature of the amines, showing the high activity of the catalyst.

Figure 8:
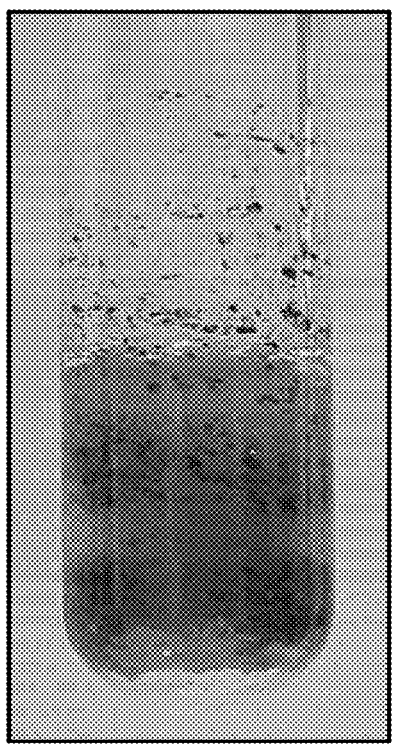
FIG. 8 depicts, according to one embodiment of the invention, the Paal-Knorr reaction of benzylamine using magnetic nanoparticle-supported glutathione in water, before completion of the reaction.
Figure 9:
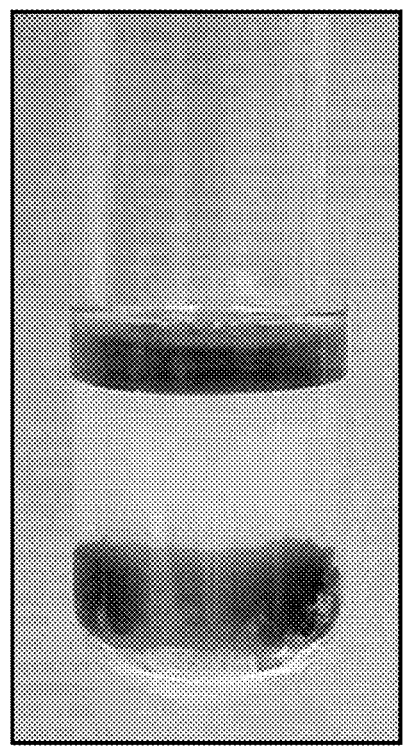
FIG. 9 depicts, according to one embodiment of the invention, the Paal-Knorr reaction of benzylamine using magnetic nanoparticle-supported glutathione in water, after completion of the reaction.

In the case of the Paal-Knorr reactions, the insoluble character coupled with paramagnetic nature enables easy separation of these nano-organocatalysts from the reaction mixture using an external magnet, which eliminates the requirement of catalyst filtration. In the Paal-Knorr reactions, the entire process was carried out in an aqueous medium without using organic solvent in the reaction or during the workout. Because of the super-paramagnetic nature of the material, within a few seconds after stirring is stopped, the nano-organocatalyst may be deposited on the magnetic bar which may be easily removed using an external magnet. Due to the selective absorption of microwaves by reactants, polar nano-organocatalyst, and the aqueous medium, these biphasic reactions functioned well in an aqueous medium without the need for any phase-transfer catalyst. After completion of the Paal-Knorr reactions, the phase separation of the desired product from the aqueous media occurred in most cases, as shown in FIG. 8 and FIG. 9. In a few cases, solid product precipitated out; the product could then be isolated by simple filtration. FIG. 9 depicts a Paal-Knorr reaction of benzylamine using magnetic nanoparticle-supported glutathione in water after completion of the reaction; FIG. 8 shows the reactants and catalyst before the reaction. As can be seen in FIG. 9, the top layer of material, the product, may be isolated by simple decantation rather than tedious extraction processes. Consequently the use of volatile organic solvents is reduced during product workup.

Figure 10:
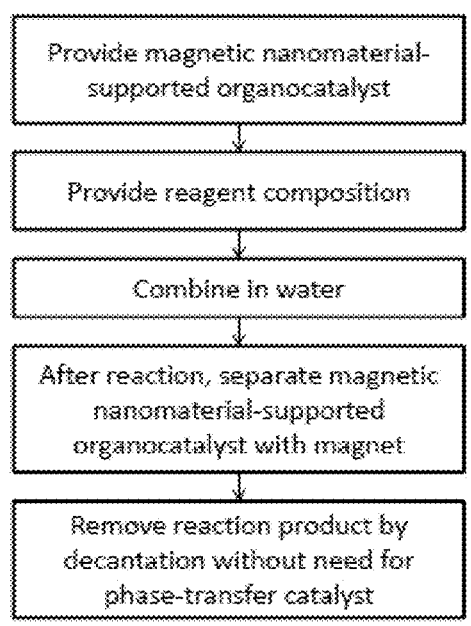
FIG. 10 depicts, according to one embodiment of the invention, steps of a method of catalyzing a reaction using a magnetic nanomaterial-supported organocatalyst.

FIG. 10 depicts, according to one embodiment of the invention, steps of a method of catalyzing a reaction using a magnetic nanomaterial-supported organocatalyst, wherein an organocatalyst is anchored to a magnetic nanomaterial. According to this embodiment, a magnetic nanomaterial-supported organocatalyst and a reagent composition are provided and combined in an aqueous solution. After the reaction, the magnetic nano-organocatalyst may be separated from the solution with a magnet. The reaction product may be removed from the solution by decantation without the need for a phase-transfer catalyst.

According to a further embodiment of the invention, the nano-organocatalyst is recyclable. For the Paal-Knorr reaction of benzylamine, the nanoparticle-supported glutathione nano-organocatalyst may be recycled five or more times without any change in activity.

Figure 6:
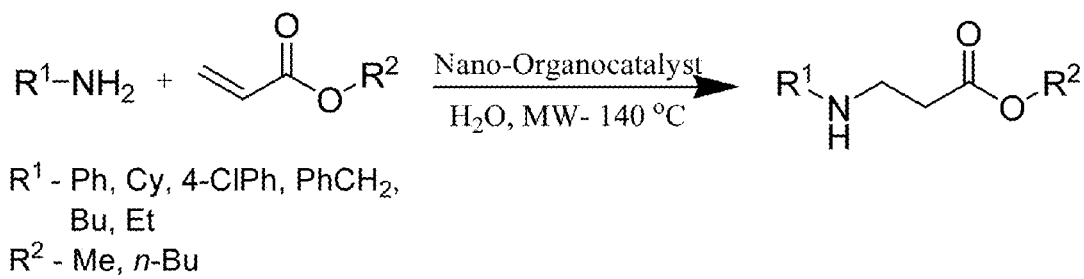
FIG. 6 illustrates nano-organocatalyst promoted aza-Michael reactions, according to another embodiment of the invention.

According to another embodiment of the invention, nano-organocatalysts are used in connection with aza-Michael addition, a vital carbon-nitrogen bond forming reaction. The nano-organocatalyst promoted aza-Michael reactions are illustrated in FIG. 6. According to another embodiment of the invention, an amine is combined with a reagent selected from the group consisting of methyl and butyl acrylate. No phase separation was observed in the aza-Michael reactions because of the high solubility of the product in water due to the presence of free —NH group.

Figure 7:
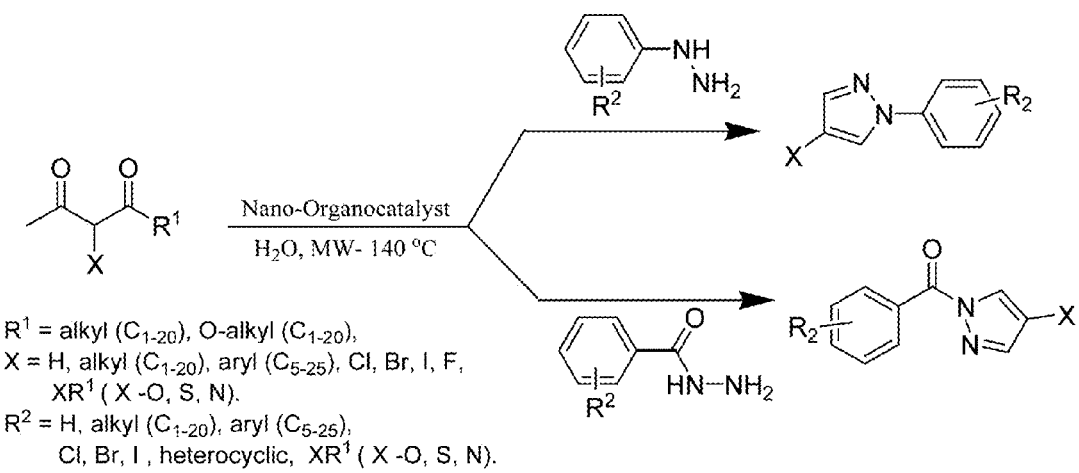
FIG. 7 illustrates nano-organocatalyst promoted pyrazole synthesis, according to another embodiment of the invention.

According to another embodiment of the invention, nano-organocatalysts are used in connection with pyrazole synthesis. The nano-organocatalyst promoted pyrazole syntheses are illustrated in FIG. 7. According to another embodiment of the invention, a reagent composition comprises a first reagent selected from the group consisting of hydrazines and hydrazides and a second reagent selected from the group consisting of diketones and β-keto esters. In the pyrazole synthesis, the product was isolated by simple decantation (in some cases) as well as extraction by ethyl acetate.

EXAMPLES

All the solvents and reagents in the Examples discussed below were purchased at the highest commercial quality and used without further purification, unless otherwise stated. Gas chromatography (GC) was used to monitor the reactions. The crude products were identified by GC-MS qualitative analysis using a GC system with a Mass selective detector.

CEM Discover focused microwave synthesis system was used to carry out all aforementioned organic transformations.

Both glutathione and cysteine were tested for Pall-Knorr reaction under homogeneous condition in water medium, to compare their catalytic activity, and glutathione appeared to be more active in comparison to cysteine. A nanoparticle-supported glutathione was used in the following Examples.

The nanoparticle-supported glutathione used in the Examples shown in Tables 1-4 (FIG. 1), was synthesized as follows: Nano-$Fe_3O_4$ (0.5 gm) was dispersed in water (15 mL) and methanol (5 mL) and sonicated for 15 minutes. Glutathione (reduced form) (0.4 gm) dissolved in water (5 mL) was added to this solution and again sonicated for 2 hours. The glutathione-functionalized nanomaterial (nano-organocatalyst) was then isolated by centrifugation, washed with water and methanol, and dried under vacuum at 50 to 60° C.

Paal-Knorr Reaction

In the Examples of Tables 1 and 2, the magnetic nanoparticle-supported glutathione described above was used in connection with the Paal-Knorr reaction.

Reaction conditions were optimized for the Paal-Knorr reaction using benzyl amine as a substrate, using the nano-organocatalyst under MW irradiation conditions. The reaction was first conducted in toluene as a reaction medium at 120° C. and a poor conversion was observed (entry 1). Increasing the reaction temperature to 140° C. provided no significant increase in conversion (entry 2). However, when the reaction was carried out in a mixture of toluene and water, good conversion was achieved (entry 3). When the reaction was carried out in pure water, 92% conversion was achieved in 20 min at 140° C. under MW irradiation (entry 5). In pure water at 140° C. under MW irradiation, 95% conversion was achieved in 30 minutes (entry 6).

TABLE 1

Optimization of reaction conditions.[a]

| No. | Solvent | R. temp. (° C.) | R. time (min) | Conversion (%) |
|---|---|---|---|---|
| 1 | Toluene | 120 | 30 | >5 |
| 2 | Toluene | 140 | 30 | >5 |
| 3 | Toluene + $H_2O$ | 140 | 30 | 80 |
| 4 | $H_2O$ | 120 | 30 | 70 |
| 5 | $H_2O$ | 140 | 20 | 92 |
| 6 | $H_2O$ | 140 | 30 | 95 |

[a] 1 mmol of benzyl amine, 25 mg of nano-organocatalyst

Deploying the above optimized reaction conditions, the scope of the magnetic nanoparticle-supported glutathione nano-organocatalyst was then investigated for Paal-Knorr reaction using a variety of amines.

In the Examples of Table 2, (A) the amines (1 mmol), (B) tetrahydro-2,5-dimethoxyfuran (1.1 mmol) and (C) nano-organocatalyst (25 mg) were placed in a 10 mL crimp-sealed thick-walled glass tube equipped with a pressure sensor and a magnetic stirrer. Water (2 mL) was added and the reaction mixture was thoroughly mixed. The reaction tube was then placed inside the cavity of a CEM Discover focused MW synthesis system, operated at 140±5° C. (temperature monitored by a built-in infrared sensor), power 50 to 250 Watt, and pressure 50 to 180 psi for 20 to 30 minutes (Table 2). After completion of the reaction, the phase separation of the desired product from the aqueous medium occurred, facilitating the isolation of crude product by simple decantation, which was further purified by simply passing through short silica column. All products are known in the literature and were identified by comparison of their GC-MS spectra with standard Wiley mass spectral library.

TABLE 2

Paal-Knorr reaction of amines using nano-organocatalyst[a]

| Entry | Substrate | Product | Yield (%) |
|---|---|---|---|
| 1 | benzylamine | 1-benzylpyrrole | 92 |
| 2 | (S)-α-methylbenzylamine | (S)-1-(1-phenylethyl)pyrrole | 90 |
| 3 | (R)-α-methylbenzylamine | (R)-1-(1-phenylethyl)pyrrole | 90 |
| 4 | 3-phenylpropylamine | 1-(3-phenylpropyl)pyrrole | 86 |
| 5 | aniline | 1-phenylpyrrole | 88 |

TABLE 2-continued

Paal-Knorr reaction of amines using nano-organocatalyst[a]

| Entry | Substrate | Product | Yield (%) |
|---|---|---|---|
| 6 | ethyl 3-aminobenzoate | ethyl 3-(1H-pyrrol-1-yl)benzoate | 85 |
| 7 | 2'-aminoacetophenone | 1-(2-(1H-pyrrol-1-yl)phenyl)ethanone | 82 |
| 8 | 2-(aminomethyl)pyridine | 2-((1H-pyrrol-1-yl)methyl)pyridine | 78 |
| 9 | benzohydrazide | N'-(1H-pyrrol-1-yl)benzohydrazide | 72 |
| 10 | benzamide | phenyl(1H-pyrrol-1-yl)methanone | NR |
| 11 | 4-nitrophenylhydrazine | 1-(4-nitrophenyl)-2-(1H-pyrrol-1-yl)hydrazine | NR |
| 12 | isobutylamine | 1-isobutyl-1H-pyrrole | 90 |
| 13 | (Z)-octadec-9-en-1-amine derivative | N-alkylpyrrole | 84 |
| 14 | 3-aminopropan-1-ol | 3-(1H-pyrrol-1-yl)propan-1-ol | 86[b] |
| 15 | propane-1,3-diamine | 3-(1H-pyrrol-1-yl)propan-1-amine | 85[b] |
| 16 | propane-1,3-diamine | 1,1'-(propane-1,3-diyl)bis(1H-pyrrole) | 72[c] |

[a]Reactions were carried out with 1 mmol of amines, 1.1 mmol of tetrahydro-2,5-dimethoxyfuran, and 25 mg of nano-organocatalyst in 1.5 ml of water at 140° C. for 20 min under MW irradiation, [b]solvent extraction was needed to isolate the product, [c]2.2 mmol of tetrahydro-2,5-dimethoxyfuran, reaction temperature 150° C., time 90 min.

As demonstrated in Table 2, the magnetic nanoparticle-supported glutathione nano-organocatalyst displayed high catalytic activity for Paal-Knorr reactions and a variety of amines reacted efficiently with tetrahydro-2,5-dimethoxyfuran to afford the desired pyrrole derivatives in good yields. The rates were barely influenced by the aliphatic or aromatic nature of the amines, showing the high activity of the nano-organocatalyst. Chiral (S)-α-methylbenzylamine and (R)-α-methylbenzylamine yielded corresponding pyrroles without racemization (entries 2 and 3). Heterocyclic amine underwent Paal-Knorr reaction with good yield of the respective pyrrole (entry 8). This protocol is also suitable for acid hydrazide (entry 9); however, attempts to use amide (entry 10) and hydrazine (entry 11) as substrates yielded no product. Significantly, substituted amines were selectively converted to pyrroles while keeping other reactive functional groups, such as ester (entry 6), ketone (entry 7), olefinic bond (entry 13), alcohol (entry 14), and amine (entry 15) intact. In the case of diamines, mono- and di-pyrrole derivatives can be synthesized just by changing the mole ratio and reaction time. For diamines, by changing the mole ratio and reaction time, mono- (entry 15) and di- (entry 16) pyrrole derivatives were obtained. These biphasic reactions functioned well in an aqueous medium without the need for any phase-transfer catalyst, which is believed to be due to the selective absorption of microwaves by reactants, polar nano-catalyst, and aqueous medium.

To evaluate lifetime and level of reusability of the catalyst, experiments were conducted using the recycled nano-organocatalyst for the Paal-Knorr reaction of benzylamine. After the completion of the first reaction, the product layer was removed by decantation and the catalyst was recovered magnetically, washed with water and methanol, and dried. A new reaction was then conducted with fresh reactants under similar conditions. It was found that the developed catalyst could be used at least 5 times without any change in activity. Alternatively, the reaction could be carried out by simply removing the product layer and adding fresh benzylamine and tetrahydro-2,5-dimethoxyfuran, and similar results were obtained.

Aza-Michael Reactions

This magnetic nanoparticle-supported glutathione nano-organocatalyst was also examined for MW-assisted aza-Michael reaction in aqueous medium as shown in FIG. 6. Using the reaction conditions developed above (140° C. under MW irradiation, 20 to 30 minutes), the scope and efficiency of this aqueous approach was explored for the reaction of various amines with methyl and butyl acrylate (Table 3). All reactions proceeded expeditiously and delivered excellent product yields. However, no phase-separation was observed in these reactions, because of the high solubility of the product in water due to the presence of free —NH group.

The amines (1 mmol) and alkyl (1.2 mmol) and nano-organocatalyst (25 mg) were placed in a 10 mL crimp-sealed thick-walled glass tube equipped with a pressure sensor and a magnetic stirrer Water (2 mL) was added and the reaction mixture was mixed thoroughly. The reaction tube was then placed inside the cavity of a CEM Discover focused MW synthesis system, operated at 140±5° C. (temperature monitored by a built-in infrared sensor), power 50 to 250 Watt, and pressure 50 to 180 psi for 20 to 30 minutes (Table 3). After completion of the reaction, products were extracted with ethyl acetate and washed with sodium bicarbonate solution. After concentrated in vacuum, the crude product was subjected to flash column chromatography for further purification. All products are known in the literature and were identified by comparison of their GC-MS spectra with standard Wiley mass spectral library.

TABLE 3

Aza-Michael addition using a magnetic nanoparticle-supported glutathione nano-organocatalyst.

| Entry | $R^1$ | $R^2$ | Product | Yield (%) |
|---|---|---|---|---|
| 1 | PhCH$_2$ | Me | 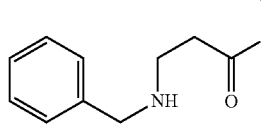 | 92 |
| 2 | PhCH$_2$ | Bu | 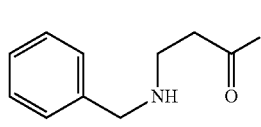 | 90 |
| 3 | Ph | Me | 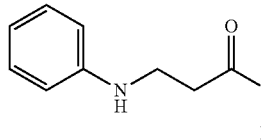 | 92 |
| 4 | Ph | Bu | 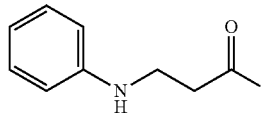 | 90 |
| 5 | Cy | Me | 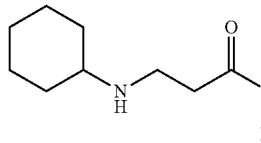 | 90 |
| 6 | Cy | Bu | 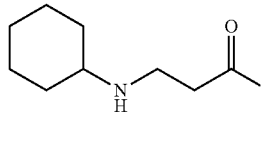 | 92 |
| 7 | 4-ClPh | Me | 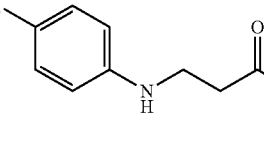 | 90 |
| 8 | 4-ClPh | Bu | 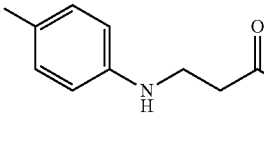 | 90 |

Pyrazole Synthesis

This magnetic nanoparticle-supported glutathione nano-organocatalyst was also examined in connection with the synthesis of pyrazole derivatives as shown in FIG. 7. Various hydrazines and hydrazides reacted efficiently with 1,3-diketones to afford the desired pyrazoles in good yields (Table 4).

The β-keto esters can also be used as a substitute for diketones in this synthesis. All these reactions proceeded efficiently in aqueous medium and were completed in 20 to 30 minutes. In some cases, the product was isolated by simple decantation, in others, it was extracted by ethyl acetate.

1.0 equiv of 1,3-diketone, 1.1 equiv of hydrazines and nano-organocatalyst (25 mg) were placed in a 10 mL crimp-sealed thick-walled glass tube equipped with a pressure sensor and a magnetic stirrer Water (2 mL) was added and the reaction mixture was mixed thoroughly. The reaction tube was then placed inside the cavity of a CEM Discover focused MW synthesis system, operated at 140±5° C. (temperature monitored by a built-in infrared sensor), power 50 to 250 Watt, and pressure 50 to 180 psi for 20 to 30 minutes (Table 3). After completion of the reaction, products were extracted with ethyl acetate and washed with sodium bicarbonate solution. After concentrated in vacuum, the crude product was subjected to flash column chromatography for further purification. All products are known in the literature and were identified by comparison of their GC-MS spectra with standard Wiley mass spectral library.

TABLE 4

Pyrazole synthesis using nano-organocatalyst

| Entry | Hydrazine | Diketone | Product | Yield (%) |
|---|---|---|---|---|
| 1 | phenylhydrazine | acetylacetone | 1-phenyl-3,5-dimethylpyrazole | 96 |
| 2 | phenylhydrazine | 3-chloro-2,4-pentanedione | 1-phenyl-4-chloro-3,5-dimethylpyrazole | 80 |
| 3 | phenylhydrazine | 3-ethyl-2,4-pentanedione | 1-phenyl-4-ethyl-3,5-dimethylpyrazole | 84 |
| 4 | 4-chlorophenylhydrazine | acetylacetone | 1-(4-chlorophenyl)-3,5-dimethylpyrazole | 82 |
| 5 | 4-chlorophenylhydrazine | 3-chloro-2,4-pentanedione | 1-(4-chlorophenyl)-4-chloro-3,5-dimethylpyrazole | 78 |
| 6 | 4-chlorophenylhydrazine | 3-ethyl-2,4-pentanedione | 1-(4-chlorophenyl)-4-ethyl-3,5-dimethylpyrazole | 84 |
| 7 | benzohydrazide | acetylacetone | 1-benzoyl-3,5-dimethylpyrazole | 88 |
| 8 | furan-2-carbohydrazide | acetylacetone | 1-(furan-2-carbonyl)-3,5-dimethylpyrazole | 84 |

In the specification and/or figures, typical embodiments of the invention have been disclosed. The present invention is not limited to such exemplary embodiments. Unless otherwise noted, specific terms have been used in a generic and descriptive sense and not for purposes of limitation.

The invention claimed is:

1. A method of catalyzing a reaction using a magnetic nanomaterial-supported organocatalyst comprising the steps of:
providing a magnetic nanomaterial-supported organocatalyst, wherein an organocatalyst is anchored to a magnetic nanomaterial;
providing a reagent composition; and
contacting the magnetic nanomaterial-supported organocatalyst with the reagent composition; and
wherein the organocatalyst comprises glutathione.

2. The method of claim 1, wherein the organocatalyst comprises a compound having a thiol group and wherein the organocatalyst is anchored to the magnetic nanomaterial through a sulfur group.

3. The method of claim 1, wherein the magnetic nanomaterial is selected from the group consisting of nano-ferrite, nano-nickel ferrite, nano-cobalt ferrite, nano-iron, and nano-cobalt and their bimetallic derivatives.

4. The method of claim 1, wherein the magnetic nanomaterial comprises nano-ferrite in the form of nanoparticles.

5. The method of claim 1, further comprising the step of separating the magnetic nanomaterial-supported organocatalyst from a reaction product with a magnet.

6. The method of claim 1, wherein the magnetic nanomaterial-supported organocatalyst and reagent composition are contacted in an aqueous medium.

7. The method of claim 6, further comprising the step of removing a reaction product by decantation without the need for a phase-transfer catalyst.

8. The method of claim 6, further comprising the step of removing a reaction product by filtration.

9. The method of claim 1, wherein the contacting step is completed to perform a Paal-Knorr reaction.

10. The method of claim 9, wherein the reagent composition comprises an amine and tetrahydro-2,5-dimethoxyfuran.

* * * * *